(12) United States Patent
Essenpreis et al.

(10) Patent No.: US 6,413,213 B1
(45) Date of Patent: Jul. 2, 2002

(54) SUBSCRIPTION BASED MONITORING SYSTEM AND METHOD

(75) Inventors: Matthias Essenpreis, Fremont, CA (US); Martin T. Gerber, Carmel; Michael V. Hansen, Fishers, both of IN (US); Christoph M. Cronrath, Lautersheim (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/551,269

(22) Filed: Apr. 18, 2000

(51) Int. Cl.$^7$ ................................................. A61B 5/00
(52) U.S. Cl. ..................... 600/300; 702/19; 204/403.04
(58) Field of Search ................................ 600/300, 301, 600/331; 128/897–925; 340/501, 502, 825.28; 713/182, 1

(56) References Cited

U.S. PATENT DOCUMENTS

| | | |
|---|---|---|
| 4,933,873 A | 6/1990 | Kaufman et al. |
| 5,053,199 A | 10/1991 | Keiser et al. |

(List continued on next page.)

FOREIGN PATENT DOCUMENTS

| | | |
|---|---|---|
| WO | WO 98/50873 | 11/1998 |
| WO | WO 99/04043 | 1/1999 |

OTHER PUBLICATIONS

HomMed, "Making a Difference in Congestive Heart Failure Care", Feb. 16, 2000, 1 page, http://www.hommed.com/HowHomMedCanhelp/Making/ADifference.asp.

HomMed, "Data Collection and Transmission", Feb. 16, 2000, 1 page, http://www.hommed.com/HowItWorks/HomMedSentry.asp.

Boehringer Mannheim Diabetes Site—Accutrend Sensor, "Blood Glucose Monitoring Systems", Feb. 16, 2000, 2 pages, http://www.diabetes.co.za/sensor.htm.

American Telecare, Inc., "Telemedicine Systems: American Telecare", Feb. 16, 2000, 4 pages, http://www.telemed-care.com/products.htm.

SNET LifeNet Solutions$^{SM}$ Home Telemonitoring Service, "LifeNet", Feb. 16, 2000, 3 pages, http://www.snet.com/business/healthca/cblitmon.htm.

*Primary Examiner*—Eric F. Winakur
*Assistant Examiner*—David J. McCrosky
(74) *Attorney, Agent, or Firm*—Bose McKinney & Evans, LLP

(57) ABSTRACT

A system (10) for subscription monitoring of a medically significant characteristic of a bodily fluid which includes a meter (12), a ROM circuit (36), a test strip (34), and a registry (50). Meter (12) has an identifier corresponding to a subscription user. ROM circuit (36) is provided with test strips (34), and contains calibration data and an identifier. The meter (12) requires an activation code before it may conduct a biosensing test. The meter (12) communicates with registry (50) through communication means (40) and provides the meter identifier and ROM circuit identifier. Registry (50) checks for valid association of the meter identifier, ROM circuit identifier, and user identifier. If a valid association is established, the registry (50) provides an activation code to the meter (12), enabling meter (12) to conduct testing during a subscription period. The meter (12) thereafter validates the ROM circuit (36) association on power up, so that ROM circuit (36) may only be used with meter (12), thereby discouraging fraudulent conveyance of ROM circuit (36) and test strips (34).

68 Claims, 8 Drawing Sheets

U.S. PATENT DOCUMENTS

| | | |
|---|---|---|
| 5,243,516 A | 9/1993 | White |
| 5,246,858 A | 9/1993 | Arbuckle et al. |
| 5,288,636 A | 2/1994 | Pollmann et al. |
| 5,339,821 A | 8/1994 | Fujimoto |
| 5,352,351 A | 10/1994 | White et al. |
| 5,366,609 A | 11/1994 | White et al. |
| 5,508,171 A | 4/1996 | Walling et al. |
| 5,627,075 A | 5/1997 | Bateson |
| 5,689,242 A | 11/1997 | Sims et al. |
| 5,710,551 A | 1/1998 | Ridgeway |
| 5,732,401 A | 3/1998 | Conway |
| 5,762,770 A | 6/1998 | Pritchard et al. |
| 5,785,650 A | 7/1998 | Akasaka et al. |
| 5,801,755 A | 9/1998 | Echerer |
| 5,827,180 A | 10/1998 | Goodman |
| 5,857,967 A | 1/1999 | Frid et al. |
| 5,899,855 A * | 5/1999 | Brown ................... 128/904 |
| 5,941,829 A | 8/1999 | Saltzstein et al. |
| 5,961,446 A | 10/1999 | Beller et al. |
| 5,966,654 A * | 10/1999 | Croghwell et al. .... 340/825.28 |
| 5,967,975 A | 10/1999 | Ridgeway |
| 5,977,817 A | 11/1999 | de la Soujeole |
| 5,987,519 A | 11/1999 | Peifer et al. |
| 5,995,937 A | 11/1999 | DeBusk et al. |
| 6,014,432 A | 1/2000 | Modney |
| 6,295,506 B1 * | 9/2001 | Heinonen et al. ........... 600/301 |

\* cited by examiner

SUBSCRIPTION BASED MONITORING SYSTEM AND METHOD

FIELD OF THE INVENTION

This invention relates to biosensing meters and test strips, and more particularly, to subscription based biosensor monitoring systems.

BACKGROUND OF THE INVENTION

Common biosensor monitoring systems for measuring a significant characteristic of bodily fluid, such as coagulation time or glucose levels, include disposable test strips for use in a biosensing meter. Particular use of such test strips has been made for measuring glucose in human blood. Such test strips have been used by diabetics and health care professionals for monitoring their blood glucose levels. The test strips are usually used in conjunction with the biosensing meter. The meter may measure light reflectance, such as specular reflection, if the strip is designed for photometric detection of a dye, or the meter may measure an electrical property, such as electrical current, if the strip is designed for detection of an electroactive compound.

In meters for calculating and displaying the results of reactions of medically significant characteristics (e.g., glucose, coagulation time) of biological sera (e.g., blood, urine or the like) on test strips, it is well known that the test strips are not precisely reproducible from batch to batch. Accordingly, calibration data must be realized for each batch of test strips and provided to the biosensing meter to obtain accurate test results. The calibration data is often provided via an electronically readable information carrier, such as a read only memory (ROM) circuit, which is plugged into a socket in the biosensing meter. The socket electronically couples the ROM circuit to a microprocessor/controller in the biosensing meter. Because the calibration data is germane to the test strip batch, the ROM circuit is provided with a vial of test strips (e.g., a quantity of 50 tests strips from the same batch) so that accurate test results may be obtained for the entire vial. Thus, upon receiving a new vial of test strips, the user inserts the new ROM circuit into the biosensing meter, and uses this same ROM circuit for the entire vial of test strips.

Biosensing meters often include a memory device to store a number of recent test results. These stored test results are used to provide trend data to the user, which is then available to a health care provider to foster better therapy decisions. The accuracy of the historical data and trend data in tracking the user's condition is dependent on the testing frequency. Thus, users may desire to conduct biosensing tests frequently.

However, the frequency of testing is directly proportional to the user's cost, as test strips are sold on a quantity basis. Thus, users often limit their testing frequency to keep their individual monitoring costs down, even though this compromises the accuracy of the historical data, trend data tracking, and predicting the users' conditions. Additionally, if the user has a contract with a reimbursement institution, such as a health insurance carrier, the reimbursement institution may also limit the number of test strips used per day. Also, many users have become visually impaired, and/or their manual dexterity has deteriorated as a result of their medical condition, resulting in test strips being damaged before or during insertion into the biosensing meter, thereby artificially inflating monitoring costs for these users.

A subscription based biosensor monitoring system provides a user with a higher testing frequency at a fixed cost. The subscription based monitoring system involves providing vials of test strips in a reasonable, but essentially unlimited, quantity to the user for a fixed subscription period cost (e.g., monthly, bimonthly, etc.). Thus, a user under a subscription agreement may more accurately track a medically significant characteristic of biological fluid (e.g., glucose, coagulation time), and thereby more accurately monitor his or her condition, at a fixed cost.

Unfortunately, existing biosensing meter technology cannot distinguish between subscription and non-subscription test media. Furthermore, existing biosensing meter technology cannot ensure that a subscription user is not giving a vial provided under subscription to a non-subscription user. As each vial is provided with a ROM circuit containing calibration data, and the ROM circuit may be used in any corresponding meter, a user could provide the entire vial and ROM circuit to a non-subscription user, or temporarily loan the vial and ROM circuit to a non-subscription user. This fraudulent activity reduces cost for the users, but drastically increases the cost for the suppliers and manufacturers of test strips sold on a subscription agreement.

Thus, there is a need for a subscription based biosensor monitoring system, and also a need for a subscription based biosensing monitoring system that is fraud resistant.

SUMMARY OF THE INVENTION

The invention provides a subscription based biosensor monitoring system and method. The invention guards against fraudulent activity by ensuring that the vial of test strips and a ROM circuit may only be used with an identified biosensing meter.

If the vial and ROM circuit are provided to a different biosensing meter, the biosensing meter will not activate.

The invention includes a system for monitoring a medically significant characteristic of a bodily fluid, the system including a biosensing meter identified as a subscription meter by a first identifier and having a controller being adapted to activate the meter upon receiving an activation code, and a test media identified as subscription test media by a second identifier, the test media associated with the biosensing meter.

The invention also includes a registry associating the first identifier to the second identifier, and providing an activation code to the controller.

Additionally included in the invention are unique first and second identifiers, the unique identifiers providing enhanced security against fraudulent activity.

The invention also includes a method for subscription monitoring of a medically significant characteristic of a bodily fluid, the method including the steps of identifying a biosensing meter as a subscription meter, identifying a test media as subscription test media, associating the identified biosensing meter to the identified test media, and activating the identified biosensing meter by the association. The step of activating the identified biosensing meter includes the steps exchanging information between the biosensing meter and a registry, and retrieving an activation code from the registry.

The method of the invention also includes uniquely identifying the biosensing meter and uniquely identifying the test media, and associating the uniquely identified biosensing meter and uniquely identified test media to a subscription user.

Another method of the invention includes uniquely identifying a biosensing meter, associating the uniquely identified biosensing meter to a particular user, uniquely identifying a set of test media, and associating the uniquely identified biosensing meter to the uniquely identified set of test media. Then, it is determined whether the particular user is an authorized subscriber, and when the particular user is an authorized subscriber, activating the uniquely identified biosensing meter for use with the uniquely identified set of test media, and monitoring the use of the uniquely identified set of test media with the uniquely identified biosensing meter by the particular user.

Additionally, a method for monitoring a medically significant characteristic of a bodily fluid includes the steps of identifying a biosensing meter as a subscription meter, establishing a subscription period, and providing a test media during the subscription period.

DETAILED DESCRIPTION OF THE INVENTION

Figure 1:
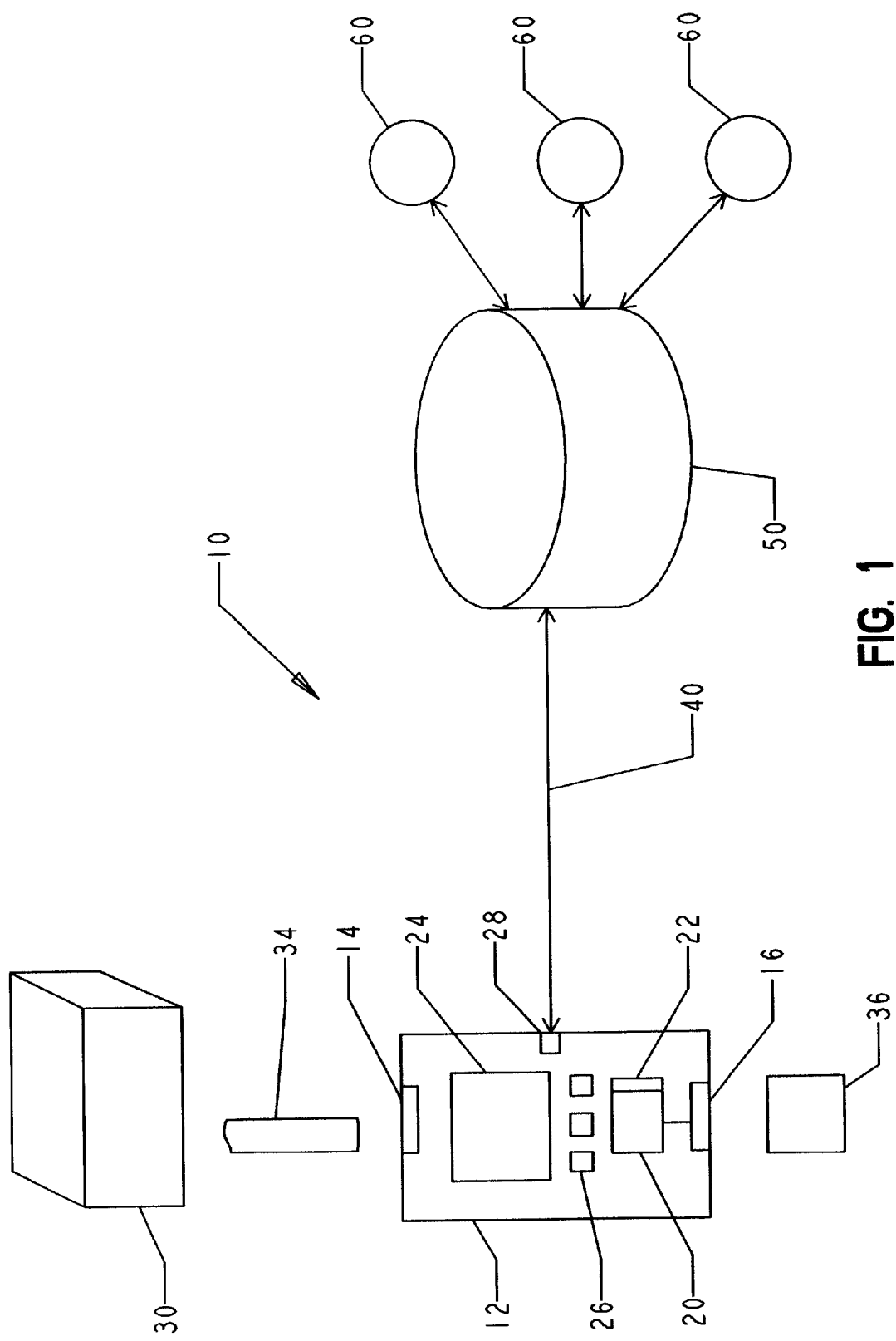
FIG. 1 is an illustrative diagram of a subscription based biosensing monitoring system.

As shown in FIG. 1, the system 10 illustratively includes a biosensing meter 12, a subscription vial 30 and an associated electronically readable information carrier, such as a ROM circuit 36, and a registry 50. The meter 12 communicates with the registry 50 through communication means 40 and communication port 28. Communication means 40 may be a phone line, a cellular link, a wireless link, or an internet connection. Data inquirers 60 receive information from registry 50 to better monitor a user's condition and implement therapy decisions.

Biosensing meter 12 illustratively includes a strip receptacle 14, a ROM receptacle 16, a controller 20, a memory 22, a display 24, keys 26, and a communication port 28. The biosensing meter 12 can be similar to the types described in U.S. Pat. Nos. 5,366,609; 5,246,858; and 5,243,516, the disclosures of which are incorporated herein by reference. Communication port 28 is used to establish a bidirectional communication link with registry 50. Memory 22 stores historical data such as accumulated test data, trend values, number of tests conducted, testing frequency, etc. Memory 22 also stores an activation code provided by registry 50, and a meter identifier. The meter is identified by a subscription/non-subscription identifier. To enhance security against fraud, the meter identifier is a unique code which uniquely identifies the meter(such as a serial number), or a combination of a subscription/non-subscription identifier and unique code. This enhancement is optional. The activation code is stored in a non-volatile memory circuit, so that the activation code is retained during a memory power interrupt, such as turning the meter 12 off and on.

ROM circuit 36 is of the type described in U.S. Pat. No. 5,053,199, the disclosure of which is incorporated herein by reference. ROM circuit 36 contains batch specific calibration data for test strips 34 provided in vial 30. ROM circuit 36 also contains an identifier that identifies the ROM circuit 36 as a subscription or non-subscription ROM circuit. To enhance system security against fraud, the ROM circuit identifier is a unique identifier. Alternatively, the unique ROM circuit identifier may contain a subscription/non-subscription field, e.g. a first field containing a subscription/non subscription identifier and a second field containing a unique identifying code. This enhancement is optional. ROM circuit 36 fits into ROM receptacle 16, thereby providing electrical communication between controller 20 and ROM circuit 36.

Registry 50 stores subscription user data including a unique subscription user identifier for each subscription user. The user identifier representing a subscription user is associated with the unique meter identifier, if a unique meter identifier is used.

The registry 50 may also store additional user information, such as name, address, and historical test data and trend analysis results. The registry 50 may also be configured to receive and store all historical and trend data stored in meter memory 22.

Test strips 34 are usually used in conjunction with the biosensing meter, and are inserted into strip receptacle 14. The test strips 34 may be designed for the photometric detection of dye, if the meter 12 measures light reflectance, such as specular reflection, or may be designed for detection of an electroactive compound, if the meter 12 measures an electrical property, such as current. The design of these types of test strips and support electronics are similar to those disclosed in U.S. Pat. Nos. 5,997,817; 5,762,770; 5,627,075; 5,508,171; and 5,288,636, the disclosures of which are incorporated herein by reference.

Test strips 34 are manufactured in large quantity batches. Because the individual components and chemicals used in the manufacturing of tests strips 34 vary slightly with each batch, test strip performance varies accordingly. Therefore, for each batch of test strips 34 manufactured, calibration data is included in ROM circuit 36 and provided to the meter controller 20 during a biosensing test. Failure to provide this calibration data will reduce the accuracy of a biosensing test, or may even yield inaccurate biosensing test results.

Figure 2:
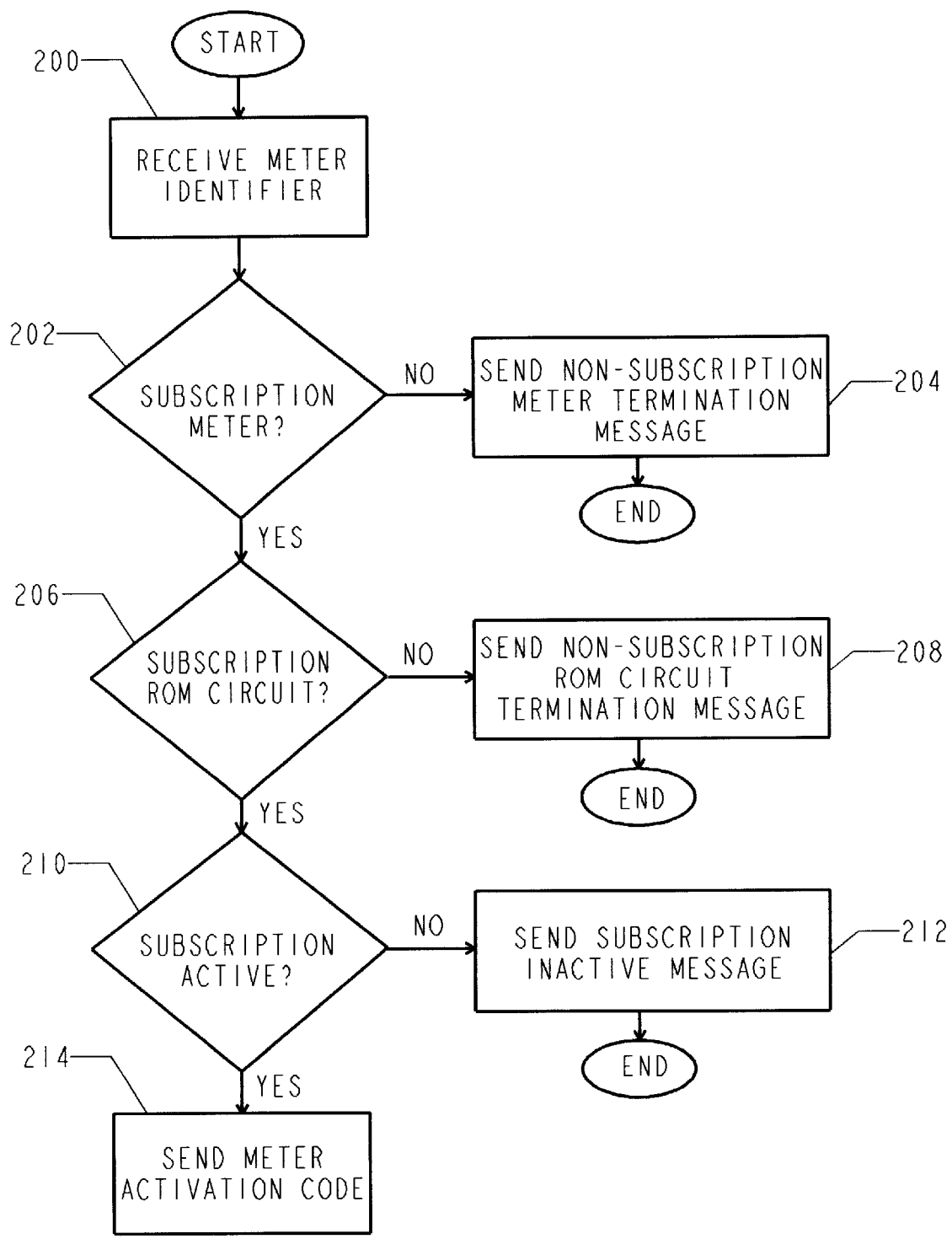
FIG. 2 is a flow diagram describing the process of obtaining a biosensing meter activation code from a registry.

In utilizing the system 10, a user receives a subscription vial 30, which contains a ROM circuit 36. At least once during use of the vial 30, the meter 12 must obtain from registry 50 an activation code. In step 200, the first step in the activation process, as shown in FIG. 2, the registry 50 receives the meter identifier. Step 202 determines from the meter identifier whether the meter 12 is a subscription meter. If the meter 12 is not a subscription meter, the registry 50 sends a non-subscription termination message, which is displayed on meter display 24, as shown in step 204.

If the meter 12 is a subscription meter, step 206 determines whether the ROM circuit 36 is a subscription ROM circuit. If the ROM circuit 36 is not a subscription ROM circuit, a non-subscription ROM circuit termination message is sent, and no activation code is provided, as shown in step 208. If the ROM circuit 36 is a subscription ROM circuit, step 210 determines whether the user's subscription is active. A user's subscription may become inactive if the user has canceled the subscription, or is overdue in a subscription payment. If the subscription is inactive, an inactive subscription message is displayed, as shown in step 212, and the meter activation code is not provided. If the subscription is active, the meter activation code is provided, and the meter 12 is enabled to conduct biosensing tests, as shown in step 214.

Figure 3:
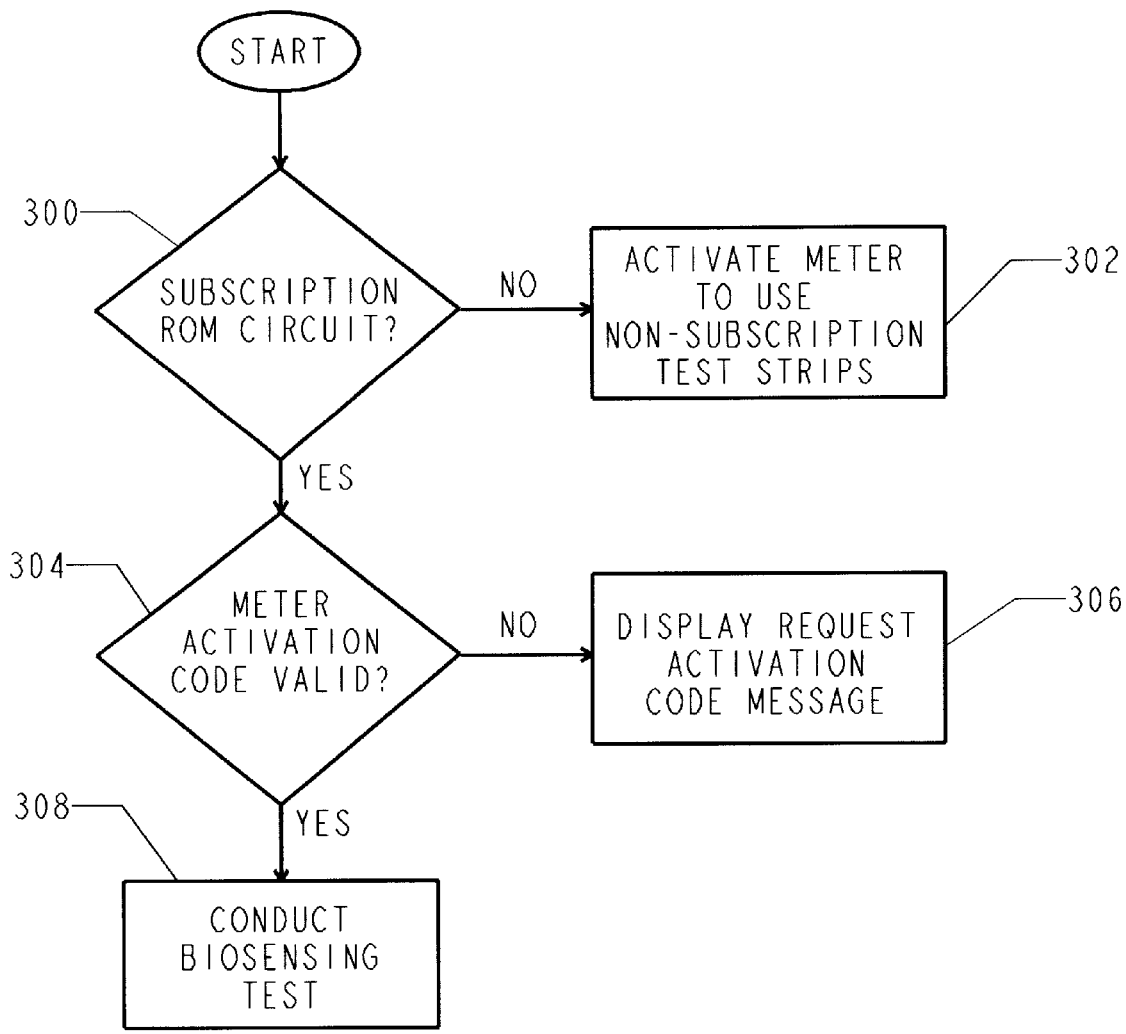
FIG. 3 is a flow diagram describing the biosensing meter power up process in which an electronically readable information carrier is verified.

After activation, the meter 12 will conduct a power-up test each time the meter 12 is energized. In step 300, as shown in FIG. 3, the meter interrogates the ROM circuit identifier to determine whether the ROM circuit 36 is a subscription ROM circuit. If the ROM circuit 36 is not a subscription ROM circuit, and the subscription agreement is non-exclusive, i.e., the meter 12 may be used with subscription or non-subscription test strips, step 302 is executed to activate meter 12 to use a non-subscription ROM circuit and test strips. Alternatively, if the subscription agreement is an exclusive agreement, i.e., the meter 12 may only be used with subscription test strips, step 302 may preclude activation of the meter 12.

If the meter 12 determines that the ROM circuit 36 is a subscription ROM circuit, the meter 12 checks memory 22 to determine whether a valid meter activation code has been received, as shown in step 304. If the activation code is invalid or has not been received, step 306 informs the user that the meter 12 must request a meter activation code from registry 50. This request is carried out in accordance with the process described in FIG. 2 and the corresponding description above.

If the meter activation code is valid, then the meter is activated to conduct a biosensing test, as shown in step 308.

To ensure compliance with a subscription period, the meter 12 checks during power up, or after each biosensing test, whether the subscription period has expired. The subscription may be a specified time period, as monitored by an internal clock in meter 12 or a specified number tests, as monitored by an internal counter in meter 12, or a combination of a specified time period and specified number of tests.

In an alternative embodiment, the activation code includes a subscription expiration date that is provided to meter 12 and monitored by an internal clock in meter 12. The subscription expiration date is the date the current subscription agreement expires, e.g., the end of the current month, the end of the current quarter, etc. This date reflects the date through which the user has paid a subscription fee. Thus, if a user obtains an activation code just before the subscription expiration date, e.g., one day, the meter 12 must obtain from registry 50 the new expiration date the next day to ensure that the user is in compliance with the subscription agreement. The meter may have a built in grace period, e.g., one subscription period, during which time the user may pay for the subscription agreement.

If a subscription period has expired due to reaching the limit of allowable tests, the meter 12 renders the ROM circuit 36 inoperable. If a subscription period has expired due to expiration of a time period, the meter 12 warns the user that a new expiration date must be obtained from the registry 50 or the ROM circuit 36 will be rendered inoperable. One method of rendering ROM circuit 36 inoperable is to manufacture ROM circuit 36 from an EEPROM and apply an electrical signal to erase the EEPROM memory contents. Another method of rendering ROM circuit 36 inoperable is to manufacture ROM circuit 36 from an EEPROM and erase an activation flag in the ROM circuit 36, while preserving the ROM circuit 36 memory contents.

Alternatively, the meter 12 includes an emergency subscription override signal that extends the subscription period for a limited time if the user is in an emergency situation and requires an immediate biosensing test. This subscription override period is limited, e.g., five biosensing tests, or one day, etc. The emergency override signal resets the activation flag in the ROM circuit 36, thus providing for limited testing.

An alternative illustrative embodiment provides data over communication means 40 in an encrypted format. Any standard point-to-point encryption method may be used, such as 64 bit encryption.

Figure 4:
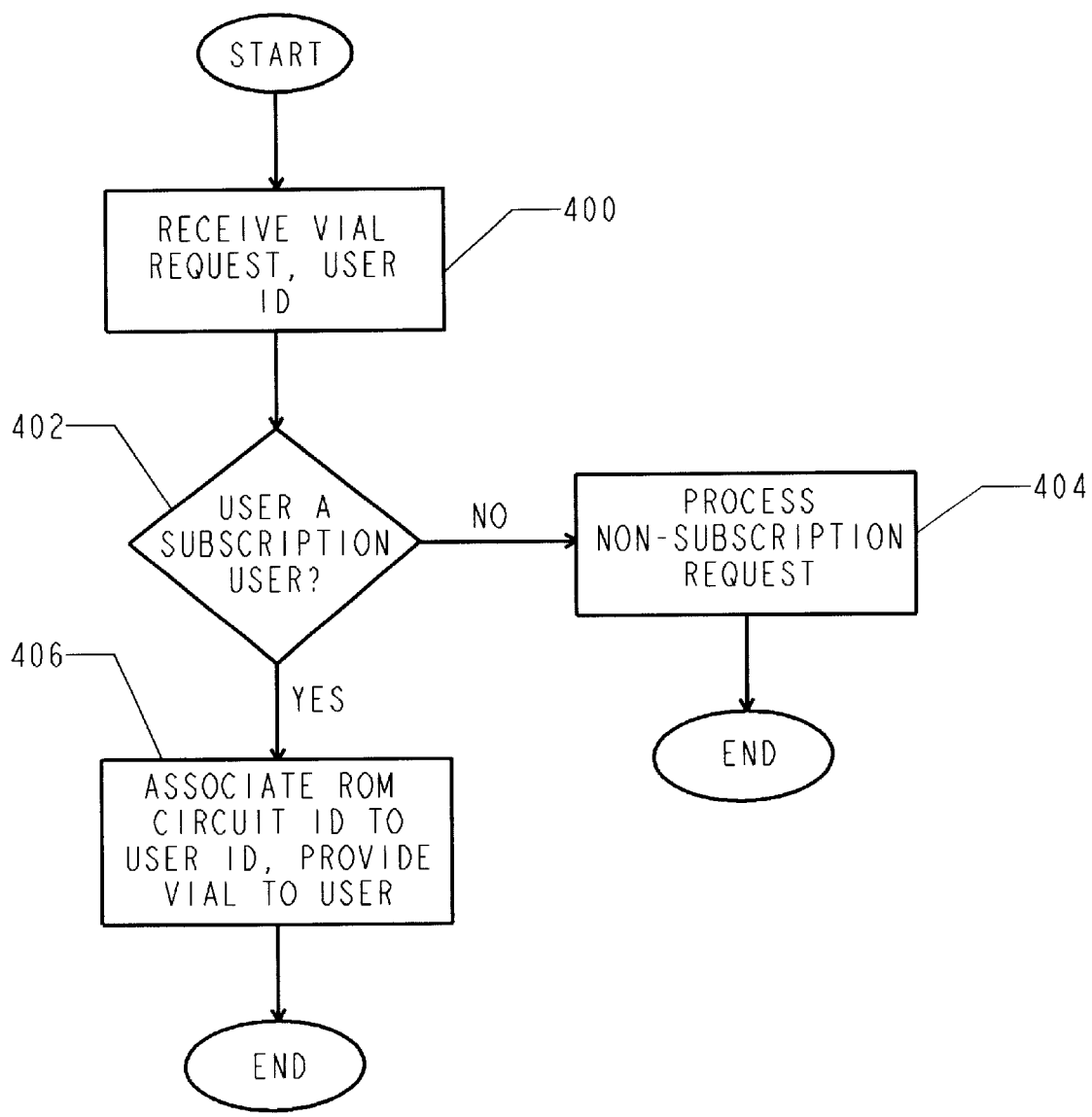
FIG. 4 is a flow diagram describing the process for associating a unique test media identifier to a subscription user to provide enhanced system security.
Figure 5:
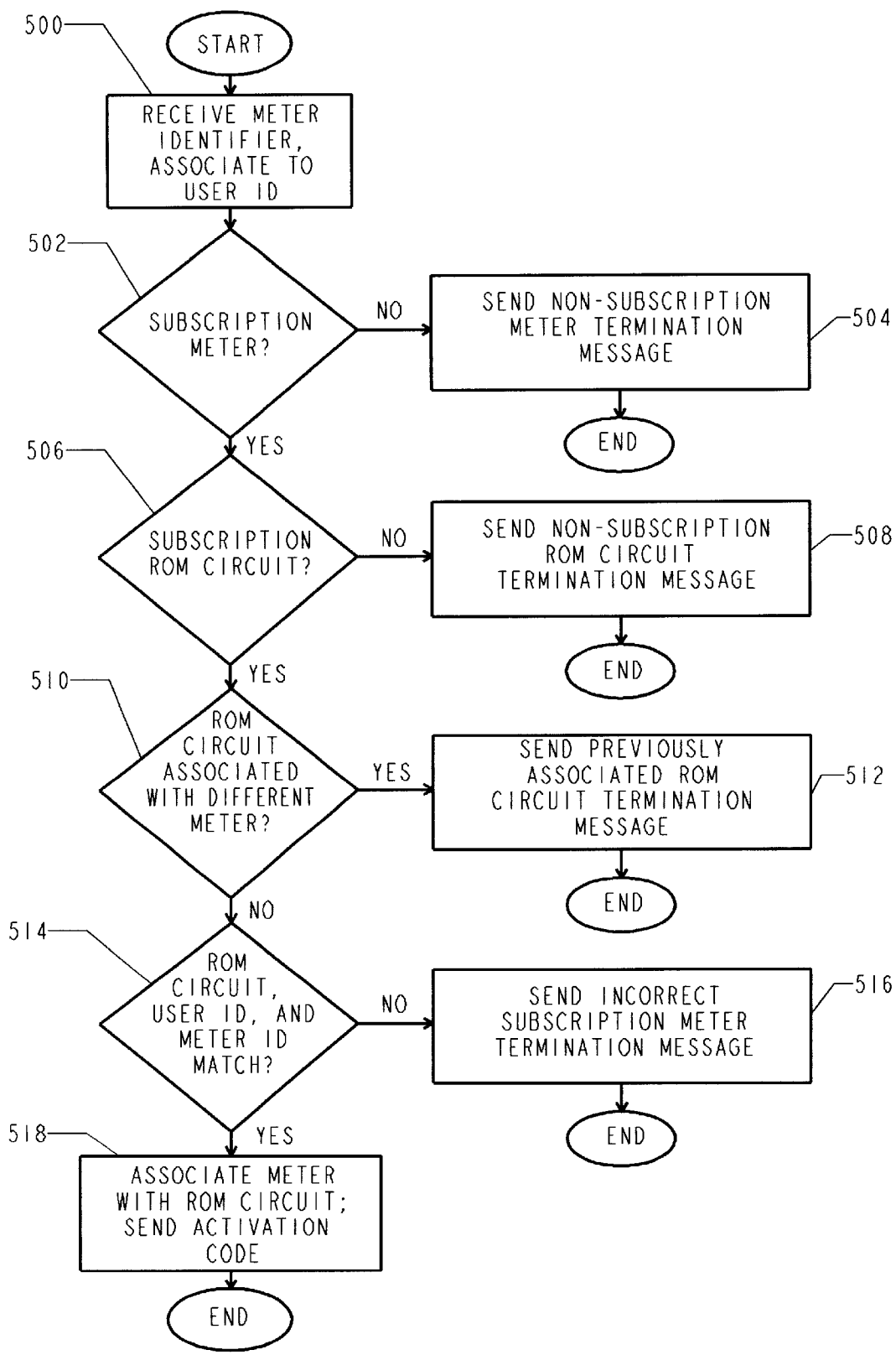
FIG. 5 is a flow diagram describing the process of obtaining the biosensing meter activation code from the registry, with security enhanced by utilizing the unique test media identifier.
Figure 6:
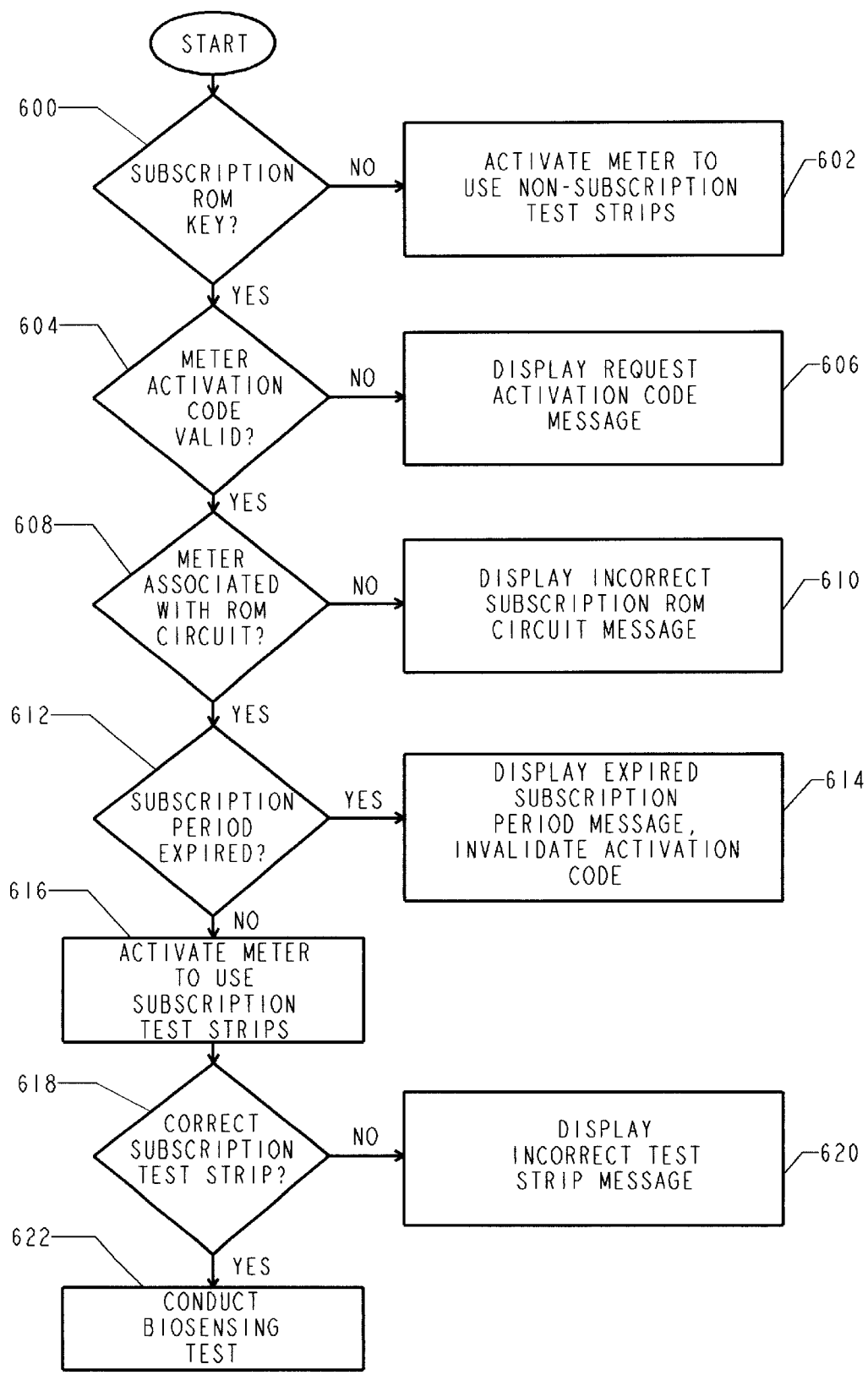
FIG. 6 is a flow diagram describing the biosensing meter power up process in which the electronically readable information carrier is verified, with security enhanced by utilizing the unique test media identifier.

Yet another alternative illustrative embodiment of the invention is provided in FIGS. 4–6. This alternative embodiment utilizes unique meter identifiers and unique test media identifiers to provide security against fraudulent activity. Thus, each meter 12 is associated with a unique meter identifier, and each ROM circuit 36 is associated with a unique ROM circuit identifier. When a user orders a vial 30 under a subscription agreement, the ROM circuit 36 is associated to the user by matching a user identifier to the unique ROM circuit identifier. The user identifier, ROM circuit identifier, and meter identifier must all correspond before the registry 50 will provide an activation code. The unique identifiers include a subscription/non-subscription identifier. Alternatively, the registry 50 may include the subscription/non-subscription identifiers in a corresponding database. Both identifying schemes are equivalent.

FIG. 4 provides a flow diagram for obtaining a subscription vial 30 in accordance with the alternative embodiment of the invention. As part of a subscription agreement, the meter 12 is associated to a specific subscription user. This association is done by associating the meter identifier to the subscription user identifier in the registry 50. Subscription users contact a subscription supplier periodically for subscription vials 30. In step 400, the registry 50 receives a request for a vial, along with the subscription user identifier. This step may be accomplished by verbal communication between the user and a registry representative, by a communication between the user and a registry over the internet, by a written request, or by an electronic link between the meter and the registry. If the user is not a subscription user, a non-subscription request is processed, as shown in step 404. Step 402 may also include the determination of whether the user's subscription has expired. If the user's subscription has expired, a non-subscription request may be processed, as shown in step 404, if the subscription agreement is non-exclusive, or, alternatively, the user is required to renew the subscription, if the subscription is exclusive. If the user is a subscription user, a subscription vial 30 is provided, and in the registry 50 the ROM circuit identifier is associated to the subscription user identifier, as shown in step 406. This association is done to ensure that the user does not provide the ROM circuit 36 and corresponding test strips from vial 30 to another user after receiving the ROM circuit 36 and vial 30, as will be explained in the description of FIG. 5 below. The subscription vial 30 and the ROM circuit 36 are then provided to the user.

Upon receipt of the subscription vial 30, the meter 12 must be activated to use the subscription ROM circuit 36. As shown in FIG. 5, this is accomplished by communicating with registry 50. In step 500, the registry 50 receives the meter identifier and associates this to the user identifier. In step 502, the registry 50 determines whether meter 12 is provided under a subscription agreement. This determination may be accomplished by having the subscription identifier included in the meter identifier, or by using the unique meter identifier to access a database in registry 50. Both are equivalent. If the determination is that the meter 12 is not a subscription meter, a non-subscription meter termination message is sent, and no activation code is provided, as shown in step 504. Step 502 may also include the determination of whether the user's subscription has expired. If the user's subscription has expired, a subscription renewal message is displayed, and the user must renew the subscription agreement before meter 12 can be activated. Alternatively, registry 50 may provide for a grace period, e.g., one subscription period, and provides a warning message to warn the user that during the grace period the user must renew the subscription agreement.

If the determination is that the meter 12 is a subscription meter, step 506 is executed. In step 506, the registry 50 determines whether ROM circuit 36 is provided under a subscription agreement. This determination may be accomplished by having the subscription identifier included in the ROM circuit identifier, or by using a unique ROM circuit identifier to access a database in registry 50. In the case of the latter, the unique ROM circuit identifier is used to access a database containing a subscription/non-subscription field. Both schemes are equivalent. If the determination is that the ROM circuit 36 is not a subscription ROM circuit, a non-subscription ROM circuit termination message is sent, and no activation code is provided, as shown in step 508.

If the determination is that the ROM circuit 36 is a subscription ROM circuit, step 510 is executed. Registry 5 accesses records indicating whether the ROM circuit 36 is associated with a different meter 12. Step 510 ensures that ROM circuits 36 that have already been used to obtain activation codes may not again be used to obtain activation codes in other meters 12, and thus prevents two different meters 12 from being able to use the same ROM circuit 36. If the ROM circuit 36 has been previously associated with a different meter 12, step 512 is executed and a previously associated termination message is sent, and no activation code is provided.

If ROM circuit 36 has not been used to obtain an activation code, step 514 is executed. Registry 50 obtains the user identifier from the user's meter identifier. The ROM circuit 36 identifier must have been previously associated to the user identifier in the registry 50 as described in the flow diagram of FIG. 4 before an activation code is sent. This step ensures that a subscription user does not order a vial 30 of test strips 34 and provide that vial to another subscription user. If the ROM circuit 36 has not been previously associated to the user identifier in the registry 50, an incorrect subscription meter message is sent, and no activation code is provided, as shown in step 516.

If the ROM circuit 36 has been previously associated to the user identifier in the registry 50, a meter activation code is sent, as shown in step 518. The meter activation code in step 518 provides data to meter 12 that associates meter 12 with ROM circuit 36. This exclusive association ensures that the ROM circuit 36 can only be used with a meter 12 that contains the unique meter identifier corresponding to the user identifier.

However, note that a meter 12 may be associated with one or more ROM circuits 36. Thus, if a user is nearing the end of a vial 30, the user does not have to wait until the vial is expended before obtaining another vial 30 pursuant to the subscription. Accordingly, a meter 12 can be used with one or more associated ROM circuits 36.

The meter activation code provides information to meter 12 that meter 12 later uses in a power up cycle to ensure that an associated ROM circuit 36 is inserted into receptacle 16 before the meter 12 will operate. The meter 12 may then be used for the subscription period as long as ROM circuit 36 is inserted into the meter. The subscription period may be a discrete time period, such as a month, or a discrete number of tests, such as a number of tests equal to the number of test strips 34 contained in vial 30. In an alternative embodiment, the activation code includes a subscription expiration date that is provided to meter 12. The subscription expiration date is the date the current subscription agreement expires, e.g., the end of the current month, the end of the current quarter, etc. This date reflects the date through which the user has paid a subscription fee. Thus, if a user obtains an activation code just before the subscription expiration date, e.g., one day, the meter 12 must obtain from registry 50 the new expiration date the next day to ensure that the user is in compliance with the subscription agreement. The meter may have a built in grace period, e.g., one subscription period, during which time the user may pay for the subscription agreement.

In order to prevent fraudulent conveyance of vials 30 and ROM circuits 36, a subscription meter 12 checks during each power up cycle the integrity of ROM circuit 36, as shown in FIG. 6. In step 600, the meter 12 interrogates the ROM circuit identifier to determine whether the ROM circuit 36 is a subscription ROM circuit. If the ROM circuit 36 is not a subscription ROM circuit, and the subscription agreement is non-exclusive, step 602 is executed to active meter 12 to use a non-subscription ROM circuit and test strips. Alternatively, if the subscription agreement is an exclusive agreement, step 602 may preclude activation of the meter 12.

If the meter 12 determines that the ROM circuit 36 is a subscription ROM circuit, the meter 12 checks memory 22 to determine whether the meter activation code is valid, as shown in step 604. If the meter activation code is invalid, step 606 informs the user that the meter 12 must request a meter activation code from registry 50. This request is carried out in accordance with the process described in FIG. 5 and the corresponding description above.

If a meter activation code is valid, step 608 determines whether the meter 12 is associated with ROM circuit 36. This is the association provided in step 518. If the meter 12 is not associated with ROM circuit 36, than an incorrect subscription ROM circuit message is displayed in accordance with step 610. This ensures that subscription vials may not be used with unauthorized meters.

If the ROM circuit 36 is associated with the meter 12, then the meter 12 determines whether the subscription period has expired, as shown in step 612. If the subscription period has expired, step 614 displays an expired subscription period message, and invalidates any activation code present in meter 12 to prevent activation of the meter 12. The activation code corresponding to the ROM circuit 36 is erased from memory 22. The user must then renew the subscription.

If the subscription period has not expired, the meter 12 is activated to use subscription test strips, as shown in step 616. Step 618 conducts a test strip integrity check to determine whether the test strip 34 matches the calibration data contained in ROM circuit 36. If the calibration data does not match, an incorrect test strip message is displayed as shown in step 620, and the test strip 34 may not be used to conduct a test. If the calibration data does match, the meter 12 is enabled to conduct a biosensing test, as shown in step 622.

Figure 7:
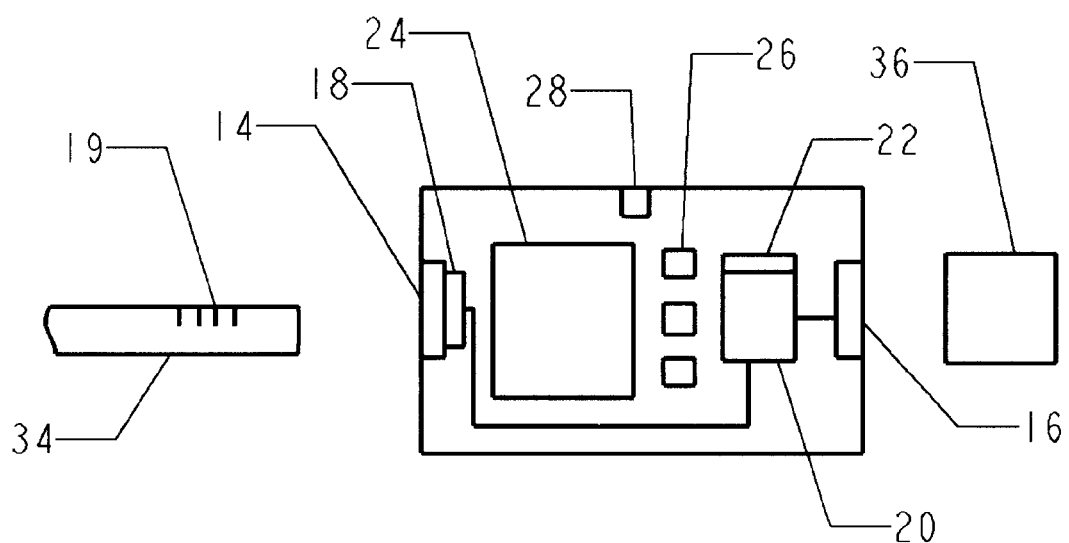
FIG. 7 is an illustrative diagram of a subscription based biosensing meter including an optical reader that reads an optical code encoded on the test strip and compares this code to an electronic code stored in the ROM circuit.

Another method of conducting the test strip integrity check of step 618 is to optically encode onto each test strip 34 in vial 30 an identifier, and to encode into ROM circuit 36 the same identifier. FIG. 7 show an illustrative embodiment. When the test strip 34 is inserted into meter 12, an optical reader 18, such as a simple bar code reader which is known in the art, reads an optical code 19 on test strip 34. Controller 20 compares this identifier to an identifier stored in ROM circuit 36. If the identifiers match, the meter 12 is enabled to conduct a biosensing test.

To ensure compliance with a subscription period, the meter 12 checks during power up, or after each biosensing test, whether the subscription period has expired. The subscription may be a specified time period, as monitored by an internal clock in meter 12, or a specified number of tests, as monitored by an internal counter in meter 12, or a combination of a specified time period and specified number of tests.

In an alternative embodiment, the activation code includes a subscription expiration date that is provided to meter 12 and monitored by an internal clock in meter 12. The subscription expiration date is the date the current subscription agreement expires, e.g., the end of the current month, the end of the current quarter, etc. This date reflects the date through which the user has paid a subscription fee. Thus, if a user obtains an activation code just before the subscription expiration date, e.g., one day, the meter 12 must obtain from registry 50 the new expiration date the next day to ensure that the user is in compliance with the subscription agreement. The meter may have a built in grace period, e.g., one subscription period, during which time the user may pay for the subscription agreement.

If a subscription period has expired due to reaching the limit of allowable tests, the meter 12 renders the ROM circuit 36 inoperable. If a subscription period has expired due to expiration of a time period, the meter 12 warns the user that a new expiration date must be obtained from the registry 50 or the ROM circuit 36 will be rendered inoperable. One method of rendering ROM circuit 36 inoperable is to manufacture ROM circuit 36 from an EEPROM and apply an electrical signal to erase the EEPROM memory contents. Another method of rendering ROM circuit 36 inoperable is to manufacture ROM circuit 36 from an EEPROM and erase an activation flag in the ROM circuit 36, while preserving the ROM circuit 36 memory contents.

Alternatively, the meter 12 includes an emergency subscription override signal that extends the subscription period for a limited time if the user is in an emergency situation and requires an immediate biosensing test. This subscription override period is limited, e.g., five biosensing tests, or one day, etc. The emergency override signal resets the activation flag in the ROM circuit 36, thus providing for limited testing.

In an alternative illustrative embodiment to that shown in FIG. 5, steps 510 and 514 are omitted. Thus, subscription vials 30 and ROM circuits 36 may be used with other subscription meters 12. While this embodiment still prevents subscription vials 30 from being used in non-subscription meters, it does not prevent two different subscription meters 12 from obtaining an activation code from one ROM circuit 36. Thus, the fraudulent activity of providing subscription vials 30 to non-subscription meters is still prevented.

Another alternative to the flow diagram of FIGS. 5 and 6 is to provide the meter activation code on the ROM circuit 36 in step 406. Embedded in the meter activation code included in ROM circuit 36 is a unique meter identifier. The meter identifier is obtained by correlating the user ID requesting the vial 30 to the meter identifier. This unique meter identifier must match the unique meter identifier of the meter 10 into which the ROM circuit 36 is inserted before the meter 10 may be activated. By embedding the meter identifier into ROM circuit 36 in step 406, the need for obtaining a separate meter activation code is eliminated. Additionally, the meter association check of step 608 during meter 10 power up is also eliminated.

It is readily apparent to one of ordinary skill in the art that any combination of unique identifiers described herein will provide added security. Thus, using only a unique meter identifier, or using only a unique test media identifier, using a combination of the unique meter identifier and unique test media identifier, and using a combination of the unique meter identifier, unique test media identifier, and unique user identifier, or any combination of these identifiers to provide added system security are within the scope of the invention.

Memory 22 of meter 12, in addition to storing relevant subscription data, also stores historical data and trend data. This data includes number of test strips used, number of tests per day, actual test data, date and time of the actual test data, etc. In an alternative embodiment, this historical data is provided to registry 50 periodically. This period may be a subscription period (e.g. monthly, bimonthly, etc.), or may be the duration of each vial (i.e., when the user contacts registry 50 to obtain an activation code), or may be an independent period not related to a subscription period or duration of each vial (e.g., weekly, bi-weekly, etc). The historical data is then used to foster better therapy decisions related to the user's condition. The data may also be provided to one or more data inquirers 60, such as a user's physician, or other qualified caregivers, so that the data inquirer 60 can better monitor the user's condition and implement therapy decisions.

If the trend data is provided to registry 50 during an activation request, an added advantage of the present invention is that the provision of this data is transparent to the user, i.e., the user does not need to periodically schedule data transmission sessions. Because these sessions are often overlooked by the user, a user's trend data available to a physician may often contain gaps and inaccuracies. Accordingly, the present invention overcomes this problem.

An alternative embodiment of the invention includes a patient management module available to physicians or caregivers. The patient management module is used to monitor the conditions of a plurality of patients, and provide the stored trend data for each patient to the central registry 50. The patient management module enables a physician to conduct biosensing test for patients under the physician's care, such as during a clinic visit or a hospitalization period, and later provide this data to the central registry for trend analysis.

Figure 8:
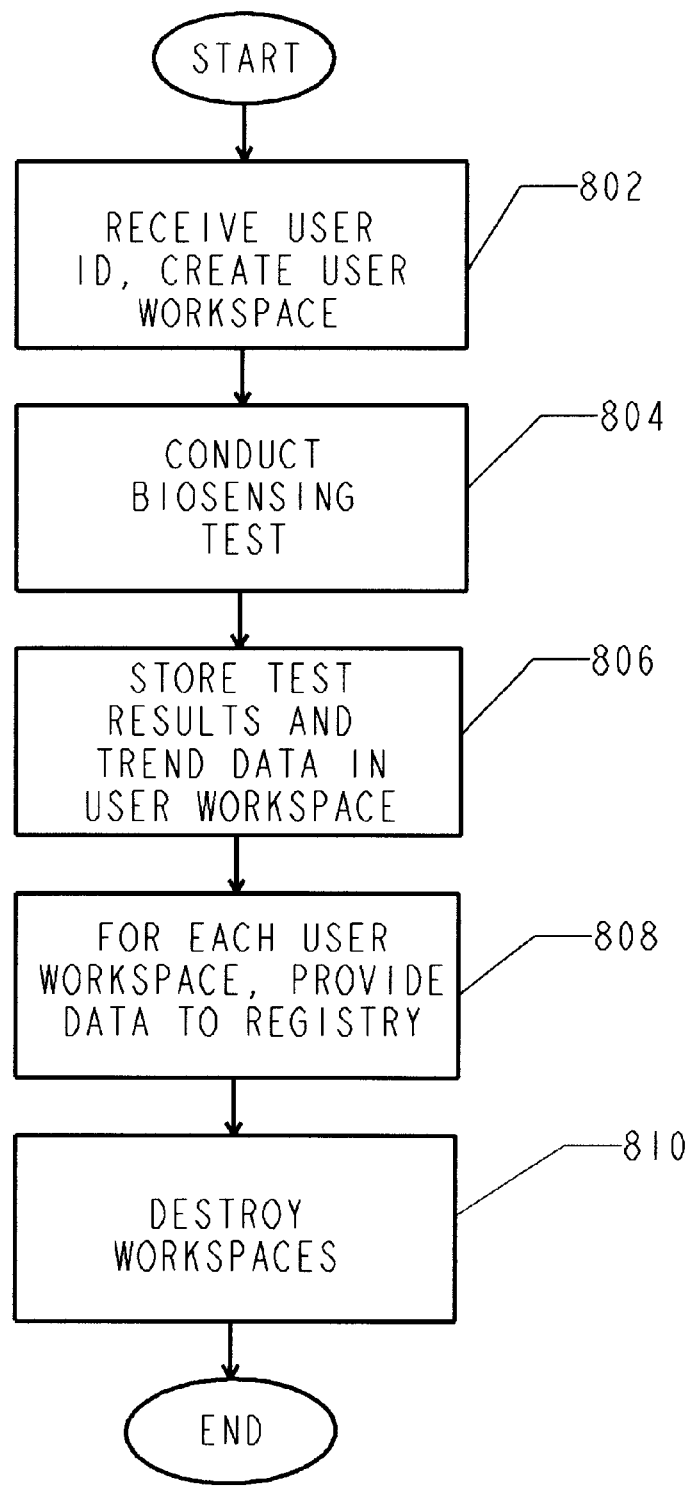
FIG. 8 is a flow diagram describing a patient management module that stores separate trend data for a plurality of users and provides this trend data to a central registry.

FIG. 8 illustrates the operation of the patient management module. In step 802, a physician provides a user identifier to the meter, and the meter creates a dynamic user work space in memory 22. The user work space is unique to the user identifier. A biosensing test is then conducted in step 804, and the results and trend data are stored in the user work space in step 806. At some later time, such as the end of the physician's work day, the physician connects to the registry 50, as shown in step 808. The meter 10 then provides the data in each user work space to the registry 50, and the historical and trend data for each user identified by a user identifier is then updated in registry 50. Step 810 destroys the user work spaces in memory 22, since retention of the data is no longer necessary.

As described, the invention provides a subscription system for users to monitor their disease condition at frequencies independent of cost. The increased frequency monitoring provides more accurate monitoring data that may be transmitted to a treatment center and/or health care provider so that more effective treatment programs tailored to a user's specific needs may be implemented. Additionally, an alternative embodiment of the invention utilizes one or more unique identifiers to prevent fraudulent activity.

The foregoing description of the invention is illustrative only, and is not intended to limit the scope of the invention to the precise terms set forth. Although the invention has been described in detail with reference to certain illustrative embodiments, variations and modifications exist within the scope and spirit of the invention as described and defined in the following claims.

What is claimed is:

1. A system for monitoring a medically significant characteristic-of a bodily fluid, the system comprising:
    a biosensing meter identified as a subscription meter by a first identifier and having a controller being adapted to activate the meter upon receiving an activation code; and
    a test media for the biosensing meter, the test media identified as a subscription test media by a second identifier, the test media and biosensing mater having a predetermined association based on the first and second identifiers.

2. The system of claim 1, further comprising a registry, the registry including a user identifier, and associating the user identifier to the first identifier.

3. The system of claim 2, wherein the registry associates the first identifier, the second identifier, and provides the activation code to the controller.

4. The system of claim 2, wherein the test media comprises an electronically readable information carrier.

5. The system of claim 4, wherein the test media further comprises a vial of test strips.

6. The system of claim 5, wherein the electronically readable information carrier includes calibration data associated with the test strips.

7. The system of claim 4, wherein the electronically readable information carrier is a read only memory (ROM) circuit.

8. The system of claim 7, wherein the controller activates the meter for a subscription period.

9. The system of claim 8, wherein the controller renders the ROM circuit inoperable after expiration of the subscription period.

10. The system of claim 9, wherein the controller includes an override code to activate the meter after a subscription period has expired.

11. The system of claim 4, wherein the electronically readable information carrier includes a meter activation code.

12. The system of claim 1, further comprising a registry, the registry associating the first identifier to the second identifier, and providing the activation code to the controller.

13. The system of claim 12, wherein the controller activates the meter for a specified time period.

14. The system of claim 13, wherein the specified time period is a subscription period.

15. The system of claim 1, wherein the controller activates the meter for a specified number of tests.

16. The system of claim 15, wherein the specified number of tests is equal to the quantity of test strips provided in a vial of test strips.

17. The system of claim 1, wherein the first identifier is a unique identifier.

18. The system of claim 17, wherein the second identifier is a unique identifier.

19. The system of claim 18, further comprising a registry, the registry including a user identifier, and associating the user identifier to the first identifier.

20. The system of claim 19, wherein the registry associates the first identifier to the second identifier.

21. The system of claim 20, wherein the registry provides the activation code to the controller.

22. The system of claim 21, wherein the controller activates the meter for a subscription period.

23. A method for subscription monitoring of a medically significant characteristic of a bodily fluid, the method comprising the steps of:
    identifying a biosensing meter as a subscription meter;
    identifying a test media;
    determining whether the identified biosensing meter is associated with the identified test media; and
    selectively activating the identified biosensing meter based on the results of the determining step.

24. The method of claim 23, further comprising the step of associating the identified biosensing meter with a unique subscriber.

25. The method of claim 23, wherein the identified biosensing meter is activated for a specified time period.

26. The method of claim 23, wherein the step of identifying a test media comprises the steps of:
    providing a vial of test strips;
    providing an electronically readable information carrier readable by the biosensing meter; and
    encoding onto the electronically readable information carrier an identifier.

27. The method of claim 26, wherein the step of identifying a test media further comprises the steps of:
    determining calibration data for the vial of test strips; and
    encoding onto the electronically readable information carrier the calibration data.

28. The method of claim 27, wherein the identified biosensing meter is uniquely identified.

29. The method of claim 28, wherein the identified test media is uniquely identified.

30. The method of claim 29, wherein the association between the uniquely identified biosensing meter and the uniquely identified test media is exclusive.

31. The method of claim 28, wherein the uniquely identified biosensing meter is activated for a specified time period.

32. The method of claim 26, wherein the step of identifying a test media further comprises the step of encoding onto the electronically readable information carrier a meter activation code.

33. The method of claim 23, wherein the identified biosensing meter is uniquely identified.

34. The method of claim 33, wherein the identified test media is uniquely identified.

35. The method of claim 34, wherein the association between the uniquely identified biosensing meter and the uniquely identified test media is exclusive.

36. The method of claim 35, wherein the step of activating the uniquely identified biosensing meter comprises the steps of:

exchanging information between the biosensing meter and a registry; and retrieving an activation code from the registry.

37. The method of claim 36, wherein the step of identifying a unique test media comprises the steps of:
providing a vial of test strips;
providing an electronically readable information carrier readable by the biosensing meter; and
encoding onto the electronically readable information carrier a unique identifier.

38. The method of claim 37, wherein the step of identifying a unique test-media further comprises the steps of:
determining calibration data for the vial of test strips; and
encoding onto the electronically readable information carrier the calibration data.

39. The method of claim 38, wherein the uniquely identified biosensing meter is activated for a specified time period.

40. The method of claim 39, further comprising the step of providing an override signal to activate the meter for an override period after the specified time period has expired.

41. The method of claim 40, further comprising the step of rendering the test media inoperative after the override period has expired.

42. A method for subscription monitoring of a medically significant characteristic of a bodily fluid, the method comprising the steps of:
uniquely identifying a biosensing meter;
associating the uniquely identified biosensing meter to a particular user;
uniquely identifying a set of test media;
associating the uniquely identified biosensing meter to the uniquely identified set of test media;
determinin whether the particular user is an authorized subscriber;
when the particular user is an authorized subscriber, activating the uniquely identified biosensing meter for use with the uniquely identified set of test media; and
when the particular user is an authorized subscriber, monitoring the use of the uniquely identified set of test media with the uniquely identified biosensing meter by the particular user.

43. The method of claim 42, wherein the step of uniquely identifying a set of test media comprises the steps of:
providing an information carrier readable by the uniquely identified biosensing meter;
associating the information carrier with the uniquely identified set of test media; and
encoding a unique identifier onto the information carrier.

44. The method of claim 42, wherein a registry associates the uniquely identified biosensing meter with the particular user and with the uniquely identified set of test media.

45. The method of claim 44, wherein the step of activating the uniquely identified biosensing meter for use with the uniquely identified set of test media when the particular user is an authorized subscriber, comprises the steps of:
establishing bidirectional communication between the uniquely identified biosensing meter and the registry;
identifying the uniquely identified biosensing meter to the registry;
determining whether the particular user associated with the uniquely identified biosensing meter is an authorized subscriber;
identifying the uniquely identified set of test media to the registry; and
pairing the uniquely identified biosensing meter with the uniquely identified set of test media.

46. The method of claim 44, wherein the step of monitoring the use of the uniquely identified set of test media with the uniquely identified biosensing meter by the particular user when the particular user is an authorized subscriber, comprises the steps of:
collecting information to be monitored using one of the uniquely identified set of test media and the uniquely identified biosensing meter;
establishing bidirectional communication between the uniquely identified biosensing meter and the registry;
identifying the uniquely identified biosensing meter to the registry;
determining whether the particular user associated with the uniquely identified biosensing meter is an authorized subscriber;
identifying the uniquely identified set of test media to the registry;
determining whether the uniquely identified biosensing meter is associated with the uniquely identified set of test media; and
when the particular user is an authorized subscriber and the uniquely identified biosensing meter is associated with the uniquely identified set of test media, reading and storing the collected information to be monitored at the registry.

47. The method of claim 46, further comprising the steps of:
establishing bidirectional communication between the registry and a data inquirer;
receiving a data request from the data inquirer to access requested registry data;
verifying the data inquirer's authorization to access the requested registry data;
when the data inquirer is authorized, communicating the requested registry data from the registry to the data inquirer.

48. A method monitoring a medically significant characteristic of a bodily fluid, the method comprising the steps of:
identifying a biosensing meter;
entering into a subscription agreement defining a subscription period; and
providing a test media for the identified biosensing meter during the subscription period.

49. The method of claim 48, wherein the biosensing meter is identified as a subscription biosensing meter.

50. The method of claim 49, wherein the test media is identified as subscription test media.

51. The method of claim 49, further comprising the steps of:
conducting biosensing tests during the subscription period; and
storing data from the biosensing tests in the biosensing meter.

52. The method of claim 51, further comprising the steps of:
establishing communication between the meter and a registry; and
providing an activation code from the registry to the biosensing meter.

53. The method of claim 52, further comprising the step of monitoring the stored biosensing test data.

54. The method of claim 53, wherein the biosensing test data is monitored by providing the biosensing test data to the registry.

55. The method of claims 53, wherein the biosensing test data is monitored by providing the biosensing test data to a health care provider.

56. The method of claim 48, further comprising the steps of:
- establishing communication between the meter and a registry; and
- providing an activation code from the registry to the biosensing meter.

57. A system for monitoring, a medically significant characteristic of a bodily fluid, the system comprising a biosensing meter including a controller configured to activate the biosensing meter upon receipt of an activation code during a subscription period defined by a subscription agreement.

58. The system of claim 57, wherein the controller includes a first identifier identifying the biosensing meter as a subscription meter.

59. The system of claim 58, further comprising a registry, the registry providing the activation code to the biosensing meter after receiving the first identifier from the biosensing meter.

60. The system of claim 58, further comprising a test media identified as subscription test media by a second identifier.

61. The system of claim 60, wherein the test media includes the meter activation code.

62. The system of claim 60, wherein the test media comprises a ROM circuit coupled to the controller.

63. The system of claim 62, wherein the test media further comprises a test strip.

64. The system of claim 63, further comprising an optical reader coupled to the controller.

65. The system of claim 64, wherein the test strip includes an optical identifying code, and wherein the ROM circuit includes an electronic identifying code.

66. The system of claim 65, wherein the optical reader is configured to read the optical identifying code.

67. The system of claim 66, wherein the controller is further configured to compare the optical identifying code to the electronic identifying code, and activate the biosensing meter based on the results of the comparison.

68. The system of claim 57, further comprising a registry, the registry providing the activation code to the biosensing meter.

* * * * *